United States Patent [19]

Markovits

[11] 4,125,440
[45] Nov. 14, 1978

[54] METHOD FOR NON-DESTRUCTIVE TESTING OF SEMICONDUCTOR ARTICLES

[75] Inventor: Gary Markovits, Poughkeepsie, N.Y.

[73] Assignee: International Business Machines Corporation, Armonk, N.Y.

[21] Appl. No.: 818,908

[22] Filed: Jul. 25, 1977

[51] Int. Cl.² ............................................. G01N 27/46
[52] U.S. Cl. .................................. 204/1 T; 204/195 R
[58] Field of Search ................. 204/1 T, 195 R, 129.3

[56] References Cited

U.S. PATENT DOCUMENTS

| | | | |
|---|---|---|---|
| 3,129,148 | 4/1964 | Steinbrecher et al. | 204/1 B |
| 3,223,598 | 12/1965 | Jacky et al. | 204/1 T |
| 3,265,599 | 8/1966 | Soonpaa | 204/129.3 |
| 3,267,014 | 8/1966 | Sanders | 204/129.3 |
| 3,366,554 | 1/1968 | Lindblad | 204/1 T |
| 3,379,625 | 4/1968 | Csabi | 204/1 T |
| 3,384,556 | 5/1968 | Rohde | 204/1 T |
| 3,408,270 | 10/1968 | Gentile | 204/1 T |
| 3,530,035 | 9/1970 | Alburger | 204/1 T |
| 3,738,917 | 6/1973 | Spath | 204/15 |
| 3,766,040 | 10/1973 | Wellborn | 204/180 R |
| 3,890,215 | 6/1975 | DiLorenzo et al. | 204/129.3 |
| 4,028,207 | 6/1977 | Faktor et al. | 204/129.3 |

OTHER PUBLICATIONS

Markovits, "IBM Technical Disclosure Bulletin," vol. 18, No. 11, Apr. 1976, p. 3623.
Edmonds et al., "IBM Technical Disclosure Bulletin," vol. 18, No. 12, p. 4012, May, 1976.

Primary Examiner—T. Tung
Attorney, Agent, or Firm—David M. Bunnell

[57] ABSTRACT

A non-destructive method of mapping damage sites in the surface of a semiconductor article, such as a silicon wafer, establishes an interface between the semiconductor and a dilute acid electrolyte. The semiconductor article is negatively biased with respect to the electrolyte and the semiconductor surface is evenly illuminated. The biasing voltage and the illumination intensity are chosen such that small hydrogen bubbles, which stick to the surface of the semiconductor article, are produced at the damage sites. The locations of the bubbles are detected and recorded.

6 Claims, 20 Drawing Figures

METHOD FOR NON-DESTRUCTIVE TESTING OF SEMICONDUCTOR ARTICLES

BACKGROUND OF THE INVENTION

A number of methods have been devised to detect damage or imperfections in monocrystalline semiconductor articles, such as silicon wafers. The detection of such imperfections is of particular interest in the manufacture of integrated circuits where imperfections in the surface layers of semiconductor substrates can reduce the yield of usable integrated circuit chips. These methods include, for example, silica bevel and etch, scanning oscillating topography, and capacitor leakage current measurements. Recently, cathodic current measurements have been employed to characterize P-type semiconductor substrates in which the substrate is placed in a dilute aqueous acid electrolyte solution and is biased a few volts negative with respect to the electrolyte. It is believed that under the influence of the electrical field, a layer of positive ions coming from the electrolyte solution develops at the semiconductor/solution interface while holes are pushed away from the semiconductor surface into the bulk of the substrate to a depth W. Only the acceptor negative ions remain in this depletion zone, and their charge equilibrates the positive charge of the ion layer at the semiconductor/solution interface. Under these conditions, if a defect generates electron/hole pairs inside the depletion zone, the holes are pushed into the bulk of the substrate by the electrical field and the electrons are drawn to the semiconductor/solution interface where they can react with the positive ions in the solution at the interface. This mechanism produces a current which can be measured outside the cell. The expected reaction between electrons and positive ions at the interface in the solution would be;

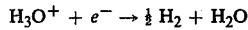

$$H_3O^+ + e^- \rightarrow \tfrac{1}{2} H_2 + H_2O$$

Because the $H_3O^+$ ion concentration is greater than that of the minority carriers at the semiconductor/solution interface the reaction is controlled by the generation rate of electron/hole pairs or, in other words, by the electrically active defects in the depletion area. The measurement of the cathodic current is then a characterization of the quality of the semiconductor substrate. THe semiconductor material is not a participant in the electrochemical reaction so that the substate is not altered. It was also noted that artificial defects in a silicon wafer could be produced by a high intensity light flash with a biasing voltage of about 5 volts. In this case when the cell was illuminated, an important gas bubbling was noticed on the wafer.

Although the cathodic current measurements are nondestructive and fast, such measurements do not give an indication of the nature or location of the defects. For example, a single large defect at one place on a semiconductor wafer and a large number of small but significant defects distributed over a relatively large area of a second wafer might give the same cathodic current. In the former case, the wafer would be suitable for integrated circuit manufacture because the damage is limited to one chip site or could even be in the Kerf area of the wafer resulting in, at most, a small loss in yield. The wafer would be considered a good wafer whereas the second wafer with a large number of small defects would be unsuitable for integrated circuit manufacture.

A method of mapping semiconductor wafer quality has been disclosed in an IBM Technical Disclosure Bulletin, Vol. 18, No. 12, May 1976, page 4012, article entitled "In-Line Wafer Quality Monitor," in which an array of light emitting diodes is employed in order to illuminate different areas of the wafer so that cathodic current information is obtained on different segments of the wafer. An IBM Technical Disclosure Bulletin, Vol. 18, No. 11, April 1976, page 3623, article entitled "Scanning Cathodic Current Spectroscopy," employs a laser to scan the semiconductor material in order to map the depletion region, with defect regions in this case producing a decrease in current, so that a map of semiconductor quality can be obtained. It is also known to locate breaks in coating layers on semiconductors or metals using an electrolyte containing biased cell so that hydrogen is produced at the places where the substrate material is exposed to the solution. Metals have been tested for stress in homogeneities by placing them in a sulfuric acid electrolyte solution at a bias of 6 volts to produce nascent hydrogen which is absorbed by the inhomogeneities. The metal surface is then covered with a plastic film and heated in order to desorb the hydrogen and form bubbles in the film at the location of the defects.

A non-destructive method of mapping damage sites on the surface of a semiconductor substrate has now been found which is rapid and which gives good correspondence to the more time consuming and/or destructive methods heretofore used to locate electrical defects in the surface of semiconductor substrates. This method is also capable of detecting defective junctions or defective portions of a large area junction.

BRIEF SUMMARY OF THE INVENTION

A method of locating electrically active damage sites in a monocrystalline semiconductor substrate comprises immersing the substrate in an electrolyte solution and uniformly illuminating the surface of the substrate with a light intensity of about 50 to 75 foot candles at the substrate surface. The substrate is negatively biased with respect to the electrolyte at a voltage level of between about 50 to 65 volts so as to produce hydrogen gas bubbles at the electrically active damage sites.

DETAILED DESCRIPTION

Figure 1:
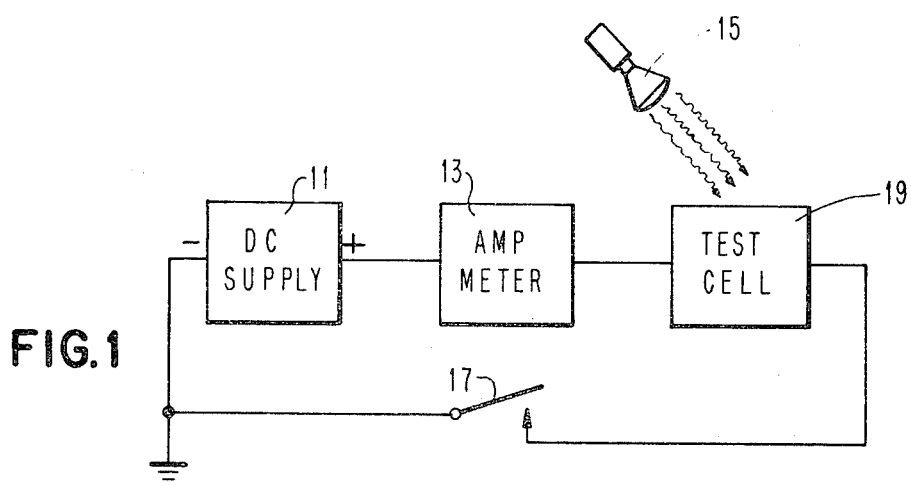
FIG. 1 is a schematic diagram of an apparatus suitable for carrying out the process of the invention.
Figure 2:
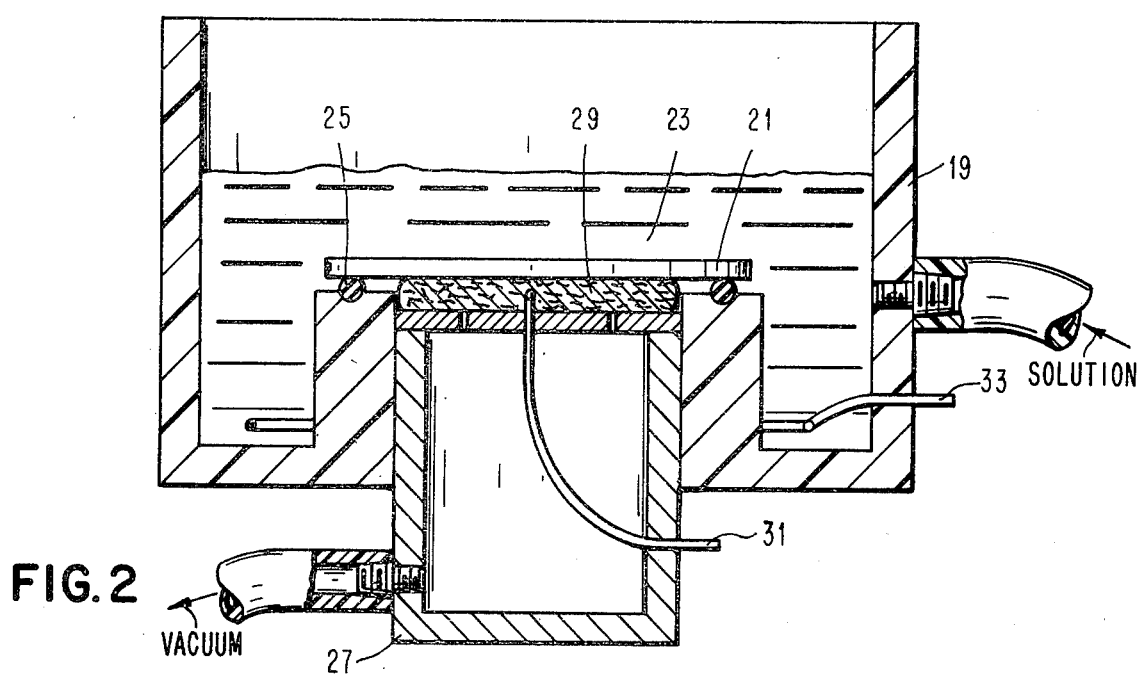
FIG. 2 is an elevational view, partially in section, of a test cell suitable for use in carrying out the process of the invention.

Turning now to FIG. 1, an apparatus suitable for carrying out the process of the invention includes DC supply 11 capable of providing up to about 65 volts, ampmeter 13, test cell 19, and a white light source 15 which will provide up to at least 80 foot candles of illumination at the wafer surface. A suitable source is a tungsten flood lamp of 75 watts. A switch 17 is also provided. The details of test cell 19, which can be of polytetrafluoroethylene, is shown in FIG. 2. Cell 19 is constructed in a way to leave one entire surface 20 of semiconductor wafer 21 exposed to the electrolyte solution 23 so that the hydrogen bubble pattern for the whole wafer can be developed at one time. Wafer 21 is mounted in cell 19 which is provided with an O-ring vacuum seal 25. Wafer 21 is held in place by vacuum chuck 27 against a graphite impregnated sponge 29 which insures a large area of uniform electrical contact to the backside of wafer 21. Sponge 29 is connected to the cathode of the DC supply by wire 31. The anode is a platinum wire 33 which extends into solution 23.

The electrolyte solution is chosen such that it will not oxidize or otherwise attack the surface of the semiconductor substrate. Dilute solutions of sulfuric acid are suitable electrolyte solutions, for example, about 1 to 2½% by volume concentrated (96%) sulfuric acid in deionized water. Other concentrations could also be used. Other electrolytes which are a source of $H_3O^+$ ions could be used such as, for example, hydrofluoric acid and acetic acid.

Materials which can be tested by the process of the invention are monocrystalline P-type semiconductor materials such as silicon or germanium and P-type semiconductor substrates having an N-type epitaxial or diffusion layer thereon. The semiconductor substrate, such as a silicon wafer, should have a surface which is clean and free of oxide. Accordingly, the substrate is first cleaned to remove any oxide, organics, or other films and dirt from the surface. Any conventional semiconductor cleaning process can be employed which will provide a clean dirt-free surface.

After cleaning, the substrate is mounted in the cell and the electrolyte is added. Care should be taken not to circulate the electrolyte during testing. This may cause the hydrogen bubbles to dislodge from the surface resulting in a loss of information. The substrate is uniformly illuminated with white light at a light intensity of from about 50 to 75 foot candles at the substrate surface. It has been found that light intensity levels below about 50 do not produce bubbling at all of the electrical defect sites but only in the most heavily damaged areas. On the other hand, intensity levels of about 80 foot candles or greater produce significant hydrogen bubbling in areas where electrical defect sites are not present. When a negative bias voltage is applied to the substrate the bubble pattern forms, the more active damage sites will bubble first with times of 1 to 15 seconds being satisfactory to develop a bubble pattern corresponding to the location of electrically active damage sites as determined by other test methods. The voltage level is important in that below about 50 volts and above about 65 volts good correspondence between the location of electrically active damage sites in the substrate and the bubble pattern is not obtained in all cases. Once the bubble pattern is developed, it can be visually observed or it can be detected and recorded by conventional photography.

The process is further illustrated by, but is not intended to be limited to the following examples.

EXAMPLE 1

Figure 3A:
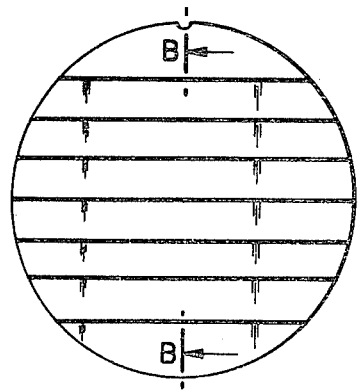
FIG. 3A is a plane view illustrating a step etched semiconductor wafer in which increasing amounts of material are removed from successive steps.
Figure 3B:
FIG. 3B is a cross-sectional view of the wafer of FIG. 3A along line B—B.

A damaged P-type 2 ohmcentimeter monocrystalline silicon wafer was step etched as illustrated in FIGS. 3A and 3B with the depth of the steps being shown in Table I.

Table I

| Step | Depth $\mu m$ |
| --- | --- |
| 1 | 0 |
| 2 | 8.5 |
| 3 | 5.0 |
| 4 | 3.5 |
| 5 | 9.5 |
| 6 | 5.0 |
| 7 | 5.0 |
| 8 | 3.0 |

The wafer was then cleaned to remove any oxide and organic films. The former can prevent bubbling and the latter can cause bubbles to form where no damage exists. The wafer was cleaned by a dip in HF followed by a 10 minute immersion in 5% sodium hypochloride with ultrasonic agitation and a rinse in deionized water. The wafer was then immersed in 10 to 1 water/HCl for 5 minutes with ultrasonic agitation, again rinsed in deionized water, and immersed 30 seconds in 10 to 1 water/HF and finally rinsed in deionized water.

Figure 4A:
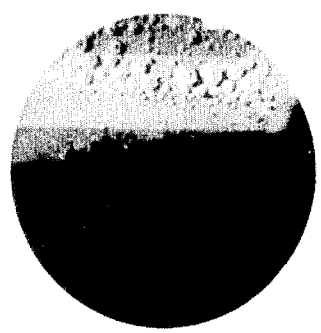
FIGS. 4A-B are photographs illustrating damage in a step etched P-type silicon wafer as determined by the process of the invention (4A) and scanning oscillating topography 4B.
Figure 4B:
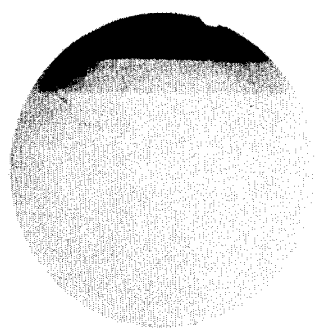

After cleaning, the wafer was placed in test cell 19 and a 2½% by volume aqueous sulfuric acid electrolyte solution was added. The lighting was provided by a 75 watt tungsten flood lamp which was adjusted to produce 70 foot candles at the wafer surface. Switch 17 was closed to provide a negative bias of 60 volts to the wafer for 5 seconds. The bubble pattern was photographed and is illustrated in FIG. 4A. It can be seen that hydrogen bubbles occur on the first four steps. A scanning oscillating topograph, which is illustrated in 4B, was obtained (see, for example, Schwuttke, "New X-Ray Diffraction Microscopy Technique for the Study of Imperfections in Semiconductor Crystals," Journal of Applied Physics, Volume 36, Number 9, September 1965, pages 2712-2721). The darker areas of the topograph indicate that damage occurs in the first four steps which corresponds to the bubble pattern test of FIG. 4A.

The wafer was then sectioned along a direction perpendicular to the steps and was beveled along the exposed edge and a dilute Sirtl etch (stock solution = 4 mil DI/1 gram $Cr_2O_3$, dilute Sirtl = 1 part stock/1 part HF) was applied to reveal the damage. The etchant is prepared by mixing one part of a stock solution of 1 gram of $Cr_2O_3$ per 4 milliliters deionized water with 1 part of HF. Starting 2 millimeters from the wafer notch, which is indicated as a V in the photograph, an optical measurement of the depth of damage was made approximately every millimeter for a total of 4 or 5 measurements per step. The results are shown in Table II below.

Table II

| Step | Bevel Section Damage Depth Microns |
|---|---|
| 1 | 36 |
|   | 36 |
|   | 34 |
|   | 34 |
| 2 | 28 |
|   | 26 |
|   | 22 |
|   | 26 |
|   | 22 |
| 3 | 16 |
|   | 16 |
|   | 16 |
|   | 16 |
|   | 14 |
| 4 | 10 |
|   | 14 |
|   | 12 |
|   | 10 |
|   | 10 |
| 5 | 0 |
|   | 0 |
|   | 0 |
|   | 0 |
|   | 0 |
| 6 | — |
|   | — |
|   | — |

It can be seen that the silica bevel and etch determination also showed damage to the first four steps so that the results indicate a good correlation between all three techniques.

EXAMPLE 2

In order to further illustrate the process of the invention, and the importance of providing the correct voltage and illumination conditions, a step etched P-type 2 ohm-centimeter, 82.5 millimeter in diameter silicon wafer was tested after slicing from a large crystal and step etching.

The depth of the steps are listed in Table III.

Table III

| Step | Depth $\mu$m |
|---|---|
| 1 | 0 |
| 2 | 5.0 |
| 3 | 5.5 |
| 4 | 6.5 |
| 5 | 5.0 |
| 6 | 7.0 |
| 7 | 7.5 |
| 8 | 8.5 |

Figure 5A:
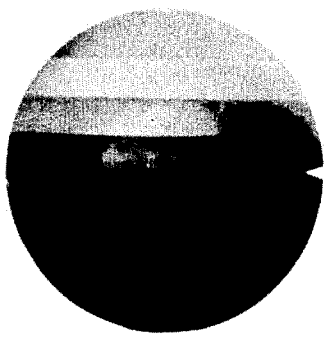
FIGS. 5A-D are photographs of a step etched silicon wafer illustrating hydrogen bubble patterns obtained at different illumination and bias voltage conditions (5A-5C) compared to a scanning oscillating topograph of the same P-type silicon wafer.
Figure 5B:
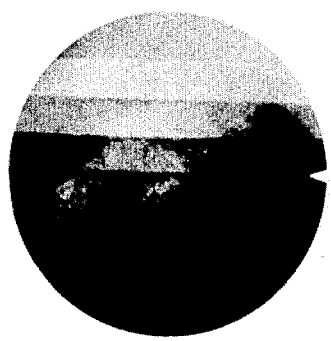
Figure 5C:
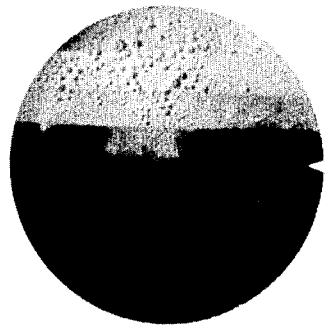
Figure 5D:
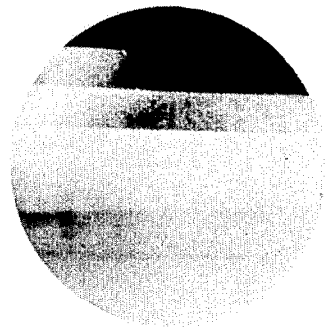

The wafer was cleaned as outlined in Example 3 below. The results obtained for several different cathodically biased conditions in test cell 19 with a 2% aqueous sulfuric acid electrolyte are shown in FIGS. 5A through 5C. The notches were cut in the photographs for orientation purposes. FIG. 5A illustrates the wafer surface after a negative bias of 5 volts was applied for 5 seconds in the dark. Only a slight mist, not visible in the photograph, was produced on the first step. The current was 18ma. The bubble pattern in FIG. 5B was obtained with a negative bias of 5 volts for 5 seconds with a 75 watt tunsten flood lamp held within 6 inches of the wafer surface to provide an illumination of greater than 250 foot candles. It can be seen that hydrogen bubbles cover almost the entire wafer, even areas indicated as damage free by the scanning oscillating topograph as shown by the light areas in FIG. 5D. The photograph in FIG. 5C was obtained using the conditions within the process of the invention with a negative bias voltage of 60 volts, an illumination of about 60 foot candles for 5 seconds. Bubbling is noted on the first four steps which is in good agreement with dark areas shown in the scanning oscillating topograph.

EXAMPLE 3

Figure 6A:
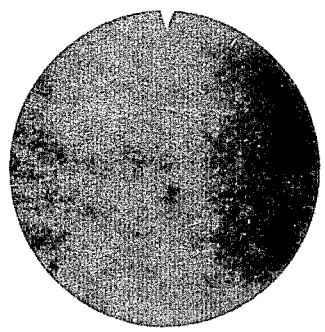
FIGS. 6A-D are photographs (6A-6C) illustrating hydrogen bubble patterns obtained at different illumination and bias voltage conditions as compared to a retouched photograph (6D) of the same P-type silicon wafer illustrating electrical defect site locations as determined by capacitor leakage current measurements.
Figure 6B:
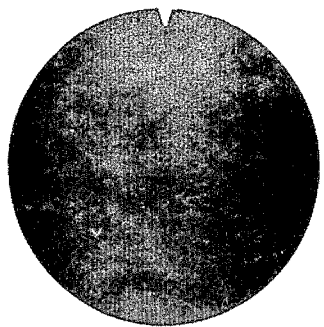
Figure 6C:
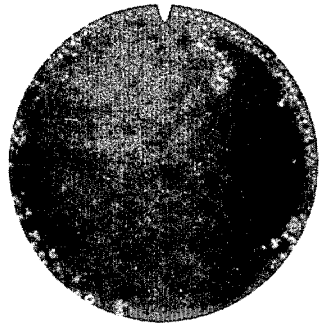
Figure 6D:
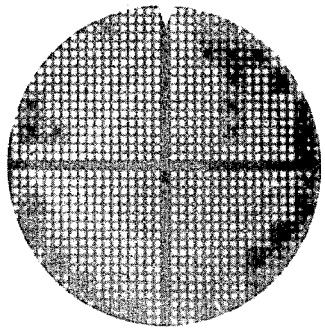

In order to illustrate the results obtained using various voltage and lighting conditions as compared to capacitor leakage current measurements, the following tests were carried out on a 2-ohm centimeter copper polished silicon substrate which was 82.5 millimeter in diameter. A 5,000 Å silicon dioxide layer was thermally grown on the substrate at 1,000° C. Aluminum dots, 60 mil in diameter, were deposited on the oxide layer and capacitor leakage currents were measured on every third dot. A map of the leakage currents which were greater than 6 nonoamps is illustrated in FIG. 6D. Because only every third dot is tested, a 9 dot array including the 8 surrounding dots was darkened with ink in the photograph whenever a tested dot exceeded 6 nonoamps. This gives an equal area weight to devices with leakage currents above or below the 6 nanoamp level. The aluminum dots were removed by an aluminum etch and the oxide stripped in HF. The substrate was cleaned by placing it in an ultrasonically agitated semiconductor detergent bath (Acationox, Sherwood Medical Industries) for 5 minutes followed by a rinse indeionized water, a 30 to 60 second dip in dilute HF (10% by volume in water) a deionized water rinse, a 1 minute soak in the detergen bath and a final water rinse.

The cleaned substrate was placed in the test cell 19 in a 2% by volume sulfuric acid solution and a negative 5 volt bias was applied for 5 seconds in the dark. The results are shown in FIG. 6A where no hydrogen formation was noted. The current was 9 ma. Next a negative bias of 5 volts for 5 seconds was applied with an illumination at the wafer surface greater than 250 foot candles. The current was 112 ma and in FIG. 6B small bubbles developed in the lower left and upper right hand quadrants of the substrate surface. It can be seen that the bubbles noted in the lower left hand quadrant of FIG. B do not correspond with the defects on the capacitor leakage current map of FIG. 6D. Next, the wafer was subjected to a 60 volt negative bias for 5 seconds with an illumination at the wafer surface of about 60 foot candles in accordance with the process of the invention. The hydrogen bubble pattern which was developed was photographed and is illustrated in FIG. 6C. It can be seen that the defect sites as determined by the bubble test (FIG. 6C) are in good correspondence with those shown in FIG. 6D where defects are noted around the perimeter of the substrate and extending into the upper right hand quadrant.

Figure 7A:
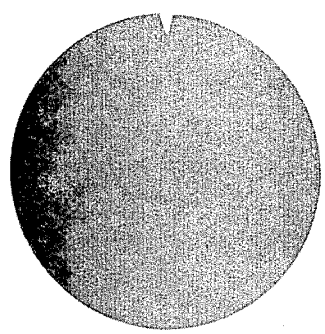
FIGS. 7A-D are photographs (7A-7C) illustrating hydrogen bubble patterns obtained at different illumination and bias voltage conditions compared to a retouched photograph (7D) of the same P-type silicon wafer illustrating electrical defect site locations as determined by capacitor leakage current measurements.
Figure 7B:
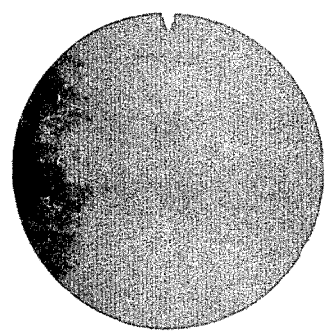
Figure 7C:
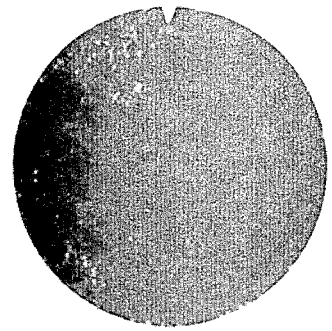
Figure 7D:
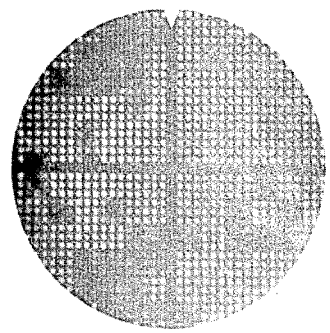

The above tests were repeated with a sample which was also a 2 ohm centimeter copper polished silicon substrate, 82.5 millimeters in diameter having a 5,000 Å thick silicon dioxide layer thermally grown at 1,000° C. Aluminum dots were deposited and capacitor leakage currents were measured on every third dot. The map of capacitor leakage currents greater than 6 nanoamps is illustrated in FIG. 7D. After stripping the aluminum and oxide, the substrate was cleaned in detergent and HF as described above. The sample was bubble tested in test cell 19 with the electrolyte being 2% volume sulfuric acid in deionized water. At a negative bias of 5 volts for 5 seconds in the dark no hydrogen formation was noted as illustrated in FIG. 7A. The current was 3 ma. At a negative bias of 5 volts for 5 seconds with an illumination at the wafer surface of greater than 250 foot candles, only a very small amount of hydrogen was formed (FIG. 7B). The current was 120 ma. Under the bubble test conditions of the invention with a negative bias of 60 volts for 5 seconds at about 60 foot candles a hydrogen bubble pattern was formed as illustrated in FIG. 7C. It can be seen that there is good correlation between the bubble pattern of FIG. 7C and that of the capacitor leakage map illustrated in FIG. 7D.

EXAMPLE 4

Figure 8A:
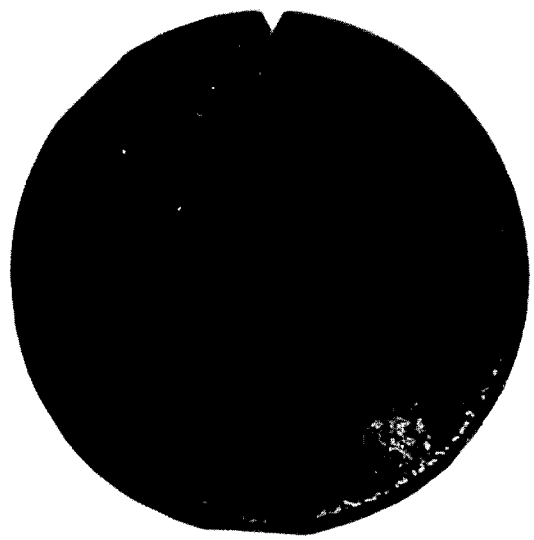
FIG. 8A is a photograph illustrating a hydrogen bubble pattern obtained for a P-type silicon wafer having an $N^+$ type subcollector region and a $N^{31}$ epitaxial surface layer using the process of the invention.
Figure 8B:
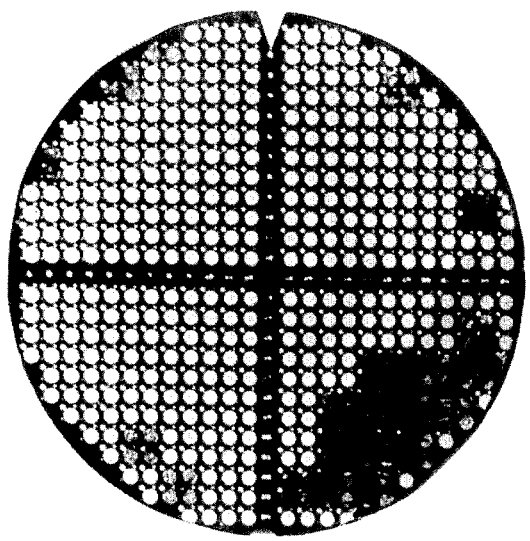
FIG. 8B is a retouched photograph of the wafer of FIG. 7A illustrating electrical defect site locations as determined by capacitor leakage current measurements.

This example illustrates the use of the process of the invention to locate electrically active defects in a P-N junction structure. A 20 ohm cm P-type silicon substrate having an $N^+$ blanket subcollector diffused region which is covered by an $N^-$ epitaxial layer was provided with an approximately 4,000 Å thick layer of thermal oxide on which aluminum dots were deposited. Capacitor leakage currents were measured and a map of the leakage currents which were greater than 6 nonoamps is illustrated in FIG. 8B. The greater than 6 nanoamp dots have been darkened with ink in the photograph.

The aluminum dots and a portion of the oxide layer were stripped from the substrate. A rim of oxide was left around the edge of the substrate which extended from the bottom to the top surface to prevent the electrolyte from electrically short circuiting the epi layer to the substrate at the wafer edges. Such a short circuit would interfere with the test. The substrate was cleaned by the procedure described in Example 3 and was placed in test cell 19. The substrate was biased at −60 volts for 1 second with an illumination of about 60 foot candles at the substrate surface. The hydrogen bubble pattern was photographed and is shown in FIG. 8A. The location of the rim of oxide at the edge of the substrate can be noted where the bubbles stop. The good correlation between the two tests can be seen, particularly the large defect area in the lower right hand quadrant of the substrate.

The foregoing has illustrated a non-destructive process for rapidly determining the electrical quality of semiconductor substrates and large area P-N junctions. It is, accordingly, easily adaptable to the requirements of integrated circuit manufacture. It provides good correlation with other tests such as scanning oscillating topography and capacitor leakage current measurements and takes only a fraction of the time. The process employes relatively simple test equipment and a record of wafer quality can be easily preserved using conventional photography. It is possible to distinguish different degrees of damage using the process of the invention by adjusting the length of time the bias is applied. The test can be employed not ony to monitor wafer quality and degree of damage after slicing, chemical thinning, and polishing, etc., but it can also be used to monitor the quality of epi growth and/or P-N junctions and to ascertain the effects of various gettering processes on electrical defects.

Although the invention has been described with reference to preferred embodiments thereof, it will be understood by those skilled in the art that the foregoing and other changes in form and details may be made therein without departing from the spirit and scope of the invention.

I claim:

1. A method of locating electrically active damage sites in a monocrystalline semiconductor substrate comprising:

immersing said substrate in a dilute electrolyte solution which is a source of $H_3O^+$ ions, illuminating the surface of said substrate with light having an intensity of from about 50 to 75 foot candles, and negatively biasing the substrate with respect to the electrolyte solution at a voltage level of from about 50 to 65 volts so as to produce hydrogen gas bubbles at the electrically active damage sites.

2. The process of claim 1 wherein the location of the hydrogen gas bubbles are photographically detected and recorded.

3. The process of claim 1 wherein the substrate comprises P-type silicon and the electrolyte comprises an aqueous acid solution.

4. The process of claim 3 wherein the electrolyte solution comprises about 1 to 2½% by volume sulfuric acid in water.

5. The process of claim 1 wherein the substrate comprises P-type silicon which has an N-type epitaxial layer formed thereon.

6. The process of claim 1 wherein the substrate is one part of a P-N junction.

* * * * *